United States Patent

Wilson et al.

[11] 4,075,204
[45] Feb. 21, 1978

[54] (1,3)DITHIOLO-(4,5-b)THIAZOLO(4',5'-e)PYRAZIN-2-YLIDENE-PROPANEDINITRILES

[75] Inventors: Charles A. Wilson; Craig E. Mixan, both of Midland, Mich.

[73] Assignee: The Dow Chemical Company, Midland, Mich.

[21] Appl. No.: 773,861

[22] Filed: Feb. 23, 1977

[51] Int. Cl.² .......................................... C07D 513/14
[52] U.S. Cl. ...................... 260/250 BC; 260/250 BN
[58] Field of Search .................................. 260/250 BC

[56] References Cited
U.S. PATENT DOCUMENTS

| 3,761,475 | 9/1973 | Kurihara et al. | 260/250 BC |
| 3,822,261 | 7/1974 | Tong | 260/250 BC |
| 3,959,277 | 5/1976 | Donald | 260/250 BC |

Primary Examiner—Alton D. Rollins
Assistant Examiner—James H. Turnipseed

Attorney, Agent, or Firm—Daniel L. DeJoseph; C. Kenneth Bjork

[57] ABSTRACT

The novel compounds corresponding to the formula

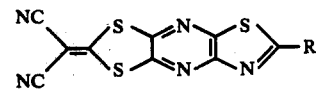

wherein R is either H or $CX_3$, with each X substituent being individually selected from the group consisting of H and X' wherein X' is either F or Cl, are prepared by reacting di(sodiomercapto)methylenemalononitrile with the corresponding 5,6-dihalothiazolo(4,5-b)pyrazine in dimethylformamide as a reaction medium at a temperature between about 0° C and about 60° C until the reaction is substantially complete. The novel compounds of the present invention have antimicrobial activity.

4 Claims, No Drawings

(1,3)DITHIOLO-(4,5-b)THIAZOLO(4',5'-e)PYRAZIN-2-YLIDENE-PROPANEDINITRILES

DESCRIPTION OF KNOWN PRIOR ART

Pyrazino-[2,3-d]-1,3-dithiole-$\Delta^{2,\alpha}$-malononitrile is disclosed in *J. Pharm. Sci.*, 57, No. 9, pp. 1611–1612 (1968). It is disclosed as having radio-protective properties.

SUMMARY OF THE INVENTION

The novel compounds of the present invention, hereinafter alternatively referred to as active compounds, correspond to the formula

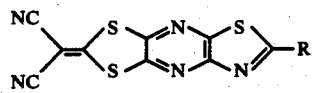

wherein R is either H or $CX_3$, with each X substituent being individually selected from the group consisting of H and X', wherein X' is either F or Cl.

These compounds are prepared by adding the corresponding 5,6-dihalothiazolo(4,5-b)pyrazine to a substantially equimolar proportion of di(sodiomercapto)-methylenemalononitrile in dimethylformamide (DMF) in accordance with the unbalanced chemical equation

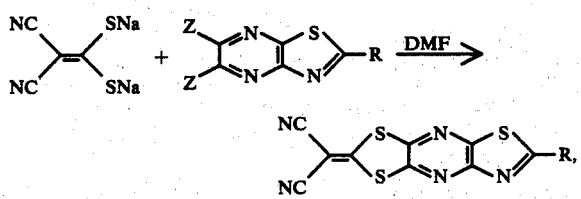

wherein R is as defined hereinbefore, and Z is either Br or Cl.

The reaction mixture is stirred from about 0° C to about 60° C until substantial completion of the reaction, usually from about 0.5 to about 20 hours. Upon completion of the reaction, the mixture is poured into ice water and the crude solid product which precipitates is recovered by filtration, washed, and dried.

The active compounds are soluble to acetone and methylene chloride and are insoluble in water.

DESCRIPTION OF THE PREFERRED EMBODIMENTS

The following examples and teachings illustrate the present invention and the manner by which it can be practiced but as such should not be construed as limitations upon the overall scope of the same. The product compounds are identified by elemental analysis and infrared spectrometry.

EXAMPLE 1

Preparation of (6-(trifluoromethyl)-(1,3)-dithiolo(4,5-b)thiazolo(4',5'-e)pyrazin-2-ylidene)-propanedinitrile To a stirred solution of 4.65 g (0.025 mol) of disodium dimercaptomethylenemalononitrile in 100 ml of dimethylformamide was added 5.8 g (0.025 mol) of 5,6-dichloro-2-trifluoromethylthiazolo(4,5-b)pyrazine. The reaction mixture was stirred in a water bath at room temperature (~25° C) for 15 hours, and was thereafter poured into 500 ml of water. The resulting solid was collected by suction filtration, washed with water and dried. The crude product was recrystallized from $CHCl_3$-hexane and dried in vacuo to yield 7 g (81% yield from the pyrazine) of a grey green solid, m.p. 214°–215° C.

Analysis — Calcd. for $C_{10}F_3N_5S_3$: C, 34.98; N, 20.38. Found: C, 35.17; N, 20.28.

Using generally similar procedures, the compounds of Examples 2 and 3, as set forth in Table 1, were prepared from the corresponding pyrazine.

TABLE 1

| | | | | Analysis Calculated | | | Analysis Found | | |
|---|---|---|---|---|---|---|---|---|---|
| Example | Product Compound | Physical Appearance | M.p. | C | H | N | C | H | N |
| 2 | (6-Methyl-(1,3)dithiolo-(4,5-b)thiazolo-(4',5'-e)pyrazin-2-ylidene)-propanedinitrile* | red brown crystals | 290° C (dec) | 41.51 | 1.04 | 24.20 | 41.40 | 1.14 | 24.20 |
| 3 | (1,3)Dithiolo-(4,5-b)-thiazolo(4',5'-e)pyrazin-2-ylidene-propanedinitrile | tan crystals | 290°C (dec) | 39.26 | 0.37 | 25.44 | 39.1 | 0.57 | 25.42 |

*washed with ethanol chloroform solution

The active compounds of the invention are useful as antimicrobials for the control of bacteria and fungi. This is not to suggest that the active compounds and mixtures thereof with usual additives are equally effective against all such organisms at the same concentration. For such uses, the active compounds can be employed in an unmodified form or dispersed on a finely divided solid and employed as a dust. Such mixtures can also be dispersed in water with the aid of a surface-active agent and the resulting emulsion employed as a spray. In other procedures, the active compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good results are obtained when employing compositions containing antimicrobial concentrations and usually from about 100 to about 500 parts by weight of one or more of the active compounds per million parts of such compositions.

Incorporation of the active compounds of this invention into material which are subject to fungal attack inhibits the growth of the fungi and preserves the original value of the materials. The active compounds are sufficiently nonvolatile and water-insoluble so that they will persist on or in such materials for long periods of time. Examples of materials which are adversely affected by fungal growth are latex and alkyl paint films, wood and wooden products. The inventive compounds are sufficiently active against fungi that only small quantities are required to prevent mildew on paint films or wood rot. The active compounds are therefore useful for long-term protection against fungal growth in or on materials having a wood basis or a protective or decorative paint film subject to fungal attack.

In representative activity tests, the active compounds are individually dispersed in warm melted nutrient agar which is then poured into petri dishes and allowed to solidify, the active compounds being employed in an amount sufficient to provide from 10 to 500 parts by weight thereof per million parts (ppm) of the ultimate agar composition. The surface of the agar is then inoculated with a variety of bacterial and fungal pest organisms, and the inoculated plates are incubated under conditions conducive to bacterial and fungal growth. Similar check plates in which the agar does not contain the active compounds or other toxic compounds are similarly inoculated and incubated.

In such operations, the active compounds gave 100% growth inhibition (kills) and control of the following organisms, as set forth in Table 2, at the indicated concentrations in parts per million: (the compounds are referred to by the Example number in which they are prepared)

TABLE 2
Antimicrobial Activity

| Organism | Concentration in ppm Compound of Example Number | | |
|---|---|---|---|
| | 1 | 2 | 3 |
| S. aureus | 500 | — | 500 |
| S. typhosa | — | 500 | — |
| B. subtilis | 500 | — | — |
| C. albicans N | 500 | 500 | — |
| C. albicans D | 500 | 500 | — |
| C. pelliculosa | 500 | — | — |
| A. pullulans | 5 | 5 | 1 |
| A. niger | 5 | 50 | 10 |
| C. ips | 5 | 10 | 5 |
| T. mentagrophytes | 5 | 50 | 10 |
| A. fumigatus | 50 | 50 | 10 |
| P. chrysogenum | 5 | 100 | 10 |
| T. Sp. P-42 | — | — | — |
| Torulopsis Sp. | 50 | — | — |

PREPARATION OF THE STARTING MATERIALS

Di(sodiomercapto)methylenemalononitrile is prepared by the method of A. Adams et al., *J. Chem. Soc.* 3061 (1959).

The 5,6-dihalothiazolo(4,5-b)pyrazine starting materials are prepared in general accordance with the following two step process:

Step 1

In a reaction vessel are mixed substantially equimolar amounts of an aminotrihalopyrazine (prepared by the procedure of G. Palamidessi and F. Luini, Farmaco Ed. Sc. 21, 811 (1966)) of the formula:

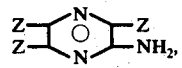

wherein Z is either Br or Cl, and sodium sulfide nonahydrate ($Na_2S \cdot 9H_2O$) in a solvent such as 2-propanol. The reaction mixture is heated to boiling under reflux for about 5 hours. After cooling, the reaction mixture is filtered, The filtrate is neutralized with hydrochloric acid and refiltered. The solid is washed with water and dried to give a 3-amino-5,6-dihalopyrazine compound of the formula

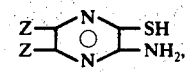

wherein Z is as defined hereinbefore.

Step 2

The 5,6-dihalothiazolo(4,5-b)pyrazine starting materials are then prepared generally in accordance with one of the following unbalanced equations:

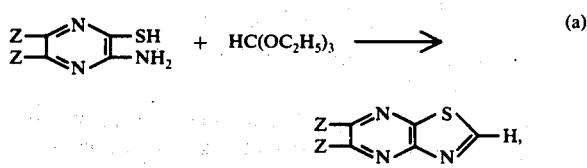

wherein Z is as defined hereinbefore.

In this reaction, the pyrazine is mixed with a molar amount excess of triethyl orthoformate in a reaction vessel. The reaction mixture is heated to boiling under reflux for from about 20 to about 25 hours, cooled to room temperature, filtered, washed with petroleum ether and dried to give the desired product.

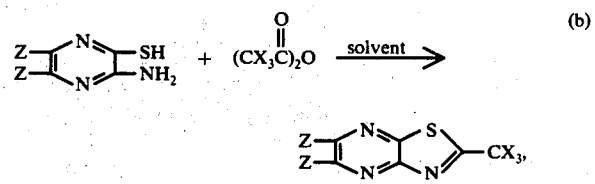

wherein Z and X are as defined hereinbefore.

In this reaction, substantially equimolar amounts of the pyrazine and the anhydride are combined with a solvent such as toluene or xylene in a reaction vessel. The reaction mixture is refluxed for about 5 to about 15 hours, cooled and the contents are taken to dryness under reduced pressure. The product is purified, such as by recrystallization from 2-propanol or methanol.

What is claimed is:

1. A compound corresponding to the formula

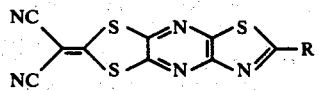

wherein R is either H or $CX_3$, with each X substituent being individually selected from the group consisting of H and X', wherein X' is either F or Cl.

2. The compound as defined in claim 1 which is (6-(trifluoromethyl)-(1,3)dithiolo-(4,5-b)thiazolo(4',5'-e)pyrazin-2-ylidene)-propanedinitrile.

3. The compound as defined in claim 1 which is (1,3)dithiolo-(4,5-b)thiazolo(4',5'-e)pyrazine-2-ylidene-propanedinitrile.

4. The compound as defined in claim 1 which is (6-methyl-(1,3)dithiolo-(4,5-b)thiazolo(4',5'-e)pyrazine-2-ylidene)-propanedinitrile.

UNITED STATES PATENT AND TRADEMARK OFFICE
CERTIFICATE OF CORRECTION

PATENT NO. : 4,075,204

DATED : February 21, 1978

INVENTOR(S) : Charles A. Wilson, Craig E. Mixan

It is certified that error appears in the above-identified patent and that said Letters Patent are hereby corrected as shown below:

Column 1, line 58 "to" should read -- in --;

Column 2, line 59 "material" should read -- materials --;

Column 3, line 22 "are" should read -- were --;

Column 3, line 66 "filtered," should read -- filtered. --;

Column 4, lines 62 and 65 "pyrazine" should read -- pyrazin --.

Signed and Sealed this

Seventh Day of November 1978

[SEAL]

Attest:

RUTH C. MASON
*Attesting Officer*

DONALD W. BANNER
*Commissioner of Patents and Trademarks*